United States Patent [19]

Christ, Jr. et al.

[11] Patent Number: 5,563,267
[45] Date of Patent: Oct. 8, 1996

[54] METHOD OF MAKING TRIALKALI AND TRIAMMONIUM SALTS OF TMT

[75] Inventors: Charles S. Christ, Jr., Fairport; Jianmin Shi, Webster, both of N.Y.

[73] Assignee: Eastman Kodak Company, Rochester, N.Y.

[21] Appl. No.: 421,585

[22] Filed: Apr. 12, 1995

[51] Int. Cl.⁶ .................................................. C07D 251/38
[52] U.S. Cl. ............................................................ 544/219
[58] Field of Search ............................................... 544/219

[56] References Cited

U.S. PATENT DOCUMENTS

| | | | |
|---|---|---|---|
| 3,428,636 | 2/1969 | Grigat et al. | 260/248 |
| 3,544,569 | 12/1970 | Schwarze et al. | 260/248 |
| 3,669,936 | 6/1972 | Regenass et al. | 260/248 |
| 3,778,368 | 12/1973 | Nakamura et al. | 210/54 |
| 4,849,517 | 7/1989 | Weber et al. | |
| 5,075,444 | 12/1991 | Hentshel et al. | 544/219 |
| 5,288,728 | 2/1994 | Spears et al. | 210/729 |

*Primary Examiner*—John M. Ford
*Attorney, Agent, or Firm*—John R. Everett

[57] ABSTRACT

A method for making trialkali metal and triammonium salts of 2,4,6 trimercapto-s-triazine comprising the steps of:

(a) forming a reaction mixture of an acetone solution of cyanuric chloride and an aqueous solution of sodium hydrosulfide hydrates;

(b) stirring the mixture thereby forming 2,4,6-trimercapto-s-triazine;

(c) acidifying the mixture to form a precipitate; and (d) dissolving the precipitate in a basic solution selected from alkali metal hydroxides and ammonium hydroxide thereby forming a trialkali metal or triammonium salt of 2,4,6 trimercapto-s-triazine.

11 Claims, No Drawings

METHOD OF MAKING TRIALKALI AND TRIAMMONIUM SALTS OF TMT

FIELD OF INVENTION

The invention relates to composition of matter for recovering metals from aqueous solutions, particularly seasoned photographic solution.

BACKGROUND OF THE INVENTION

The commercial processing of photographic materials produces seasoned (used) solutions containing silver ions. Environmental regulations restrict the discharge of solutions containing silver to concentrations much less than the silver concentrations generally found in seasoned solutions. Thus the silver concentrations in seasoned solutions must be greatly reduced before discharge into the environment.

A much improved precipitation process for removal of silver from seasoned silver containing solutions is disclosed in U.S. Pat. No. 5,288,728. A trisodium salt of mercapto-s-triazine (TMT) is used to precipitate silver. It is believed that this salt is made according to method described in U.S. Pat. No. 5,075,444. The use of this salt in silver recovery provides an improvement over the prior art. Undesirable precipitates form in trisodium TMT solutions during storage. This requires filtration. This is a particular problem when making 15% trisodium TMT solutions from commercially available 55% trisodium TMT solids. Moreover, the commercially available material has an obnoxious sulfide odor.

No other alkali metal salts of TMT are available commercially. The method of U.S. Pat. No. 5,075,444 has not been used to make such other salts of TMT. It is believed that the method of this patent will only yield salts having an obnoxious sulfide odor.

SUMMARY OF THE INVENTION

The present invention provides a method for making trialkali metal and triammonium salts of 2,4,6 trimercapto-s-triazine comprising the steps of:
  (a) forming a reaction mixture of an acetone solution of cyanuric chloride and an aqueous solution of sodium hydrosulfide hydrates;
  (b) stirring the mixture thereby forming 2,4,6-trimercapto-s-triazine as a precipitate;
  (c) acidifying the mixture; and
  (d) dissolving the precipitate in a basic solution selected from alkali metal hydroxides and ammonium hydroxide thereby forming a trialkali metal or triammonium salt of 2,4,6 trimercapto-s-triazine.

This method provides soluble TMT salts that are substantially free of sulfide impurity thereby avoiding obnoxious sulfide odors. Unlike commercially available Trisodium TMT, after several months storage no precipitate is observed in the solutions, so that problems associated with removing the undesirable precipitate are avoided. Avoidance of the precipitate prevents solution pumping problems associated with the metal recovery process.

DETAILS OF THE INVENTION

Generally the method for making trialkali metal and triammonium TMT salts can be described as follows:

An acetone solution containing cyanuric chloride is added to an aqueous solution sodium hydrosulfide hydrate to form a reaction mixture with vigorous stirring. A precipitate of 2,4,6 trimercapto-s-triazine forms. During addition of the cyanuric chloride containing solution, the reaction temperature is kept at or below the boiling point of the mixture, about 60° C. The reaction mixture is stirred at 60° C. until the reaction is complete. Temperatures in excess of 25° C. are necessary to achieve the desired product in a reasonable yield, and temperatures of at least 50° C. are preferred with the best reaction temperature of about 60° C. The reaction mixture is then cooled to room temperature and an acid containing aqueous solution is added to complete formation of the precipitate. A number of different acid containing solutions may be used, but inorganic mineral acids such as hydrochloric acid are preferred. The precipitate is filtered. Washing of the solid is not necessary, but is recommended to remove any occluded impurities. The wet precipitate is dissolved directly into a base solution chosen from any alkali metal base or ammonium hydroxide. This results in a soluble trialkali metal or triammonium TMT salt. Bases other than alkali metal bases may be used, but the most useful TMT salts result from dissolution of the solid in alkali metal bases. The base concentration may be varied to achieve the desired TMT salt concentration. A second filtration step is necessary to obtain a completely homogeneous solution, but may be omitted depending on the final application. The resulting solution can be used in the recovery of a number of transition and heavy metals as insoluble TMT salts.

The following example illustrates how the above described general procedure of the invention is carried out.

Example 1

Synthesis of Tripotassium TMT

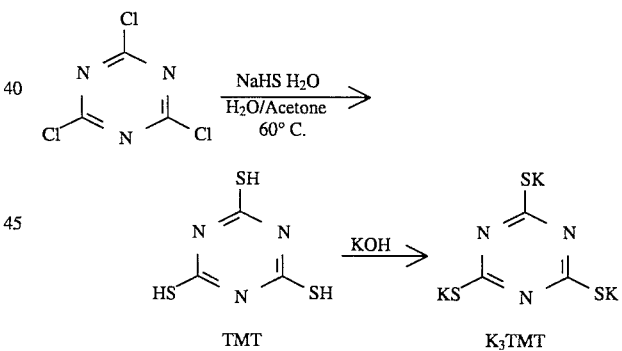

To 60 ml of aqueous solution of sodium hydrosulfide hydrate (24.2 g, 0.33 mol, Aldrich, Lot 06509JF) was slowly added 100 ml of acetone solution containing cyanuric chloride (18.4 g, 0.1 mol). A precipitate of TMT formed. The reaction temperature was controlled by rate of addition of the cyanuric chloride solution. After addition the reaction mixture was heated to 60° C. for half hour with stirring. The reaction mixture was then cooled to room temperature and 200 ml of 0.5% hydrochloric acid was added. The precipitate was filtered. The precipitate was dissolved in 70 g of 30% of potassium hydroxide solution to form tripotassium TMT. The resulted pale yellow solution was filtered. The filtrate was diluted to 200 g by adding water. The thus obtained tripotassium TMT solution can be used directly for metal recovery particularly silver recovery from aqueous solutions.

The first step in the recovery of silver from seasoned photographic solutions, and in particular from a mixture of such solutions that includes a seasoned photographic stabilizer solution, is carried out by contacting the mixture with a mercapto-s-triazine compound. Silver present in solution forms a water-insoluble complex with the mercapto-s-triazine compound.

In general, the precipitation is carried out in a pH range of about 4 to about 14, and practically from about 5 to about 8. A higher pH is preferred because the silver-compound of mercapto-s-triazine (hereinafter "silver complex") is less soluble at a higher pH and will precipitate more readily. The pH may be adjusted by conventional means to suit the operator.

The salt form of the mercapto-s-triazine compounds are preferred for the process of the invention for their increased solubility compared to their acid form. The mercapto-s-triazine compound can be provided in solid (powdered) form or in the form of an aqueous suspension or an aqueous solution for contacting the seasoned solutions. A preferred mercapto-s-triazine compound is the trisodium salt of mercapto-s-triazine, which is sold by Degussa under the product name "TMT -15".

The amount of mercapto-s-triazine used to contact the mixture of seasoned solutions can be determined based on the concentration of silver ion in the mixture. Generally, it is desirable to use in excess of the stiochiometric quantity ratio of the compound to the silver concentration, as may be seen from the examples below. The concentration of silver in the mixture of seasoned solutions can first be determined by means of conventional analytical methods, for example, photometry, potentiometry, or atomic absorption spectroscopy. The operator can also make a best estimate based on the knowledge of the seasoned solutions and the proportions of each such solution present. For example, a bleach-fix solution that is removed from a minilab tank after the system has reached a substantially steady state condition can have a reasonably predictable silver concentration. Using the trisodium salt of trimercapto-s-triazine, a preferred amount is from about 1 mole to about 3 moles per 3 moles of silver in the mixture of seasoned solutions undergoing treatment, and particularly preferred is from about 1.5 moles to about 2.0 moles per 3 moles of silver. The ratio is provided per 3 moles of silver since each molecule of trimercapto-s-triazine is capable of complexing 3 silver ions.

The method of the invention is applicable to silver recovery in photoprocessing minilabs. In such labs typically 5 to 10 gallons per day of silver-bearing photoeffluent is generated. The silver concentration ranges from 1 to 4 g/L.

The method is also applicable as a secondary silver recovery method for large photofinishers. In the latter case a large proportion of the silver has been previously recovered by a primary recovery method such as electrolysis.

The method also provides a secondary silver recovery method for large photofinisher operating in a batch-mode recovery process. After being subjected to the process of this invention, the top layer is decanted for discharge or for additional filtration, if necessary. The sludge layer is removed from the bottom of the vessel and sent to a refiner where the silver is recovered.

The seasoned photographic processing solutions from which silver can be recovered include stabilizers, fixers, bleach fixers, processing overflows containing such materials and mixtures of such processing solutions.

For both minilabs and large photoprocessing operations the method is generally applied as follows:

1. The silver containing solution is provided.
2. A mercapto-s-triazine compound, such as the trisodium salt of trimercapto-s-triazine is mixed with the solution to maximize precipitation of silver ion, thereby forming a two phase mixture of precipitate and liquid. The salt is generally mixed in liquid form (15 % by weight trimercapto-s-triazine) at a dosage of approximately 6 to 8 mL per gram of silver in solution. Equipment available from KODAK for this process provide means to mix the trimercapto-s-triazine solution with the photographic solution in batch-mode in a vessel or in-line in a continuous flow operation.
3. Mixing a flocculant, according to this invention, into the above mixture at a concentration of at least 10 mg/L, preferably 30 to 50 mg/L. The flocculant causes growth and agglomeration of precipitated fines. This reduces the number of fines in the mixture.
4. After a short period of rapid mixing subsequent to the addition of the flocculant, the mixture is mixed at a slower rate to allow precipitated particles to grow larger. In Kodak equipment configuration disclosed in previously mentioned U.S. patent application Ser. No. 08/206,335 filed Mar. 4, 1994, and incorporated herein by reference, this is accomplished by a tubular reactor coil through which the mixture passes. In this embodiment, the particles continue to grow, and the liquid portion of the two-phase mixture exhibits little or no evidence of suspended fine particles.
5. The mixture is filtered in a filter apparatus. The reduction in fine suspended particles enables the filtration of a considerable volume of seasoned solutions before the filters are clogged.
6. The concentration of silver in the filtrate is typically below 1 mg/L.
7. The silver-bearing sludge collected on the filter may be sent to a refiner for silver recovery.

Particularly useful copolymer flocculants are disclosed in U.S. Ser. No. 08/281,382 filed Jul. 27, 1994, and incorporated herein by reference. Addition of the flocculant to give a flocculant concentration of 10 to 100 ppm in the precipitated silver mixture results in the agglomeration of the insoluble silver mercapto-s-triazine fines, formation of larger more easily separated particles and simultaneous reduction of colloidal silver precipitate. Preferred concentrations are between 15 and 60 ppm, and the best concentration is from 30 to 50 ppm. Larger concentrations of flocculant may be useful to some degree but are not optimum for the purpose described here. Useful commercially available copolymer flocculants include materials from Calgon under the trade names POL-E-Z-2406; E-2280; E-2272; E-2267.

The tripotassium TMT was used in a silver recovery process according to the following example.

EXAMPLE 2

A silver bearing minilab effluent mixture was treated with the inventive tripotassium TMT ($K_3TMT$) reagent solution to precipitate silver from the effluent. The effluent was made from the following combination of solutions:

| | |
|---|---|
| KODAK FLEXICOLOR Fixer | 13.9% |
| KODAK FLEXICOLOR Stabilizer LF | 16.8% |
| KODAK EKTACOLOR PRIME Bleach-Fix | 21.0% |
| KODAK EKTACOLOR PRIME Stabilizer | 48.3% |

The $K_3TMT$ solution assay indicated that the reagent solution contained approximately 9.3% $K_3TMT$ by weight.

The density of the solution was measured by weighing two samples of volume 10 and 20 ml and the density was determined to be 1.15 g/ml.

Various amounts of the K$_3$TMT reagent solution were added to the minilab effluent to determine the efficacy of the precipitation with various dosages. For each dosage experiment, a square glass vessel was charged with 500 ml of the minilab effluent (2.2 g/l silver) and a flat 3"×1" paddle stirring prop was used to agitate the solution at approximately 180 RPM. The K$_3$TMT solution was added to the effluent and a yellow precipitate was formed. After 15 seconds 10 ml of flocculating agent were added (giving a final flocculant concentration of 30 ppm) and stirring was continued at 180 RPM for another 15 seconds. After initial mixing of the flocculant the stirring rate was decreased to 100 RPM for 30 seconds and further reduced to 20 RPM for 1 additional minute. In each case a large floc was formed and settled to the bottom of the vessel and a clear solution was obtained. Approximately 20 ml of solution were filtered through a 0.45 micron disk filter and submitted for silver analysis. To determine the silver concentration before filtration, a second sample was removed from final solution obtained in TEST 4 (see 4a.) Of the four tests performed, TEST 4 involved the lowest dosage of K$_3$TMT and represents the worst case scenario for silver removal. The results of the variable dosage experiment are summarized below:

| TEST # | Dosage* (% excess) | Final Silver Concentration |
| --- | --- | --- |
| 1. | 100 | <0.3 ppm |
| 2. | 75 | <0.3 ppm |
| 3. | 50 | 0.3 ppm |
| 4. | 25 | 0.6 ppm |
| 4a. | 25 | Unfiltered 1.8 ppm |

Dosage is based on the ideal precipitate stoichiometry, Ag$_3$TMT, i.e. 0% excess is 3:1, moles Ag to moles K$_3$TMT.

In each test the final silver concentration after filtration is less than 1 ppm and clearly shows the efficacy of the new K$_3$TMT precipitating agent for removal of silver from a representative photoprocessing solution. In addition, the results also show that the new K$_3$TMT precipitating agent works extremely well in conjunction with the flocculating agent disclosed in U.S. patent application Ser. No. 08/281,382.

The invention has been described in detail with particular reference to preferred embodiments thereof, but it will be understood that variations and modifications can be effected within the spirit and scope of the invention.

We claim:

1. A method for making trialkali metal and triammonium salts of 2,4,6 trimercapto-s-triazine comprising the steps of:

(a) forming a reaction mixture of an acetone solution of cyanuric chloride and an aqueous solution of sodium hydrosulfide hydrates;

(b) stirring the mixture thereby forming 2,4,6-trimercapto-s-triazine as a precipitate;

(c) acidifying the mixture; and (d) dissolving the precipitate in a basic solution selected from alkali metal hydroxides and ammonium hydroxide thereby forming a trialkali metal or triammonium salt of 2,4,6 trimercapto-s-triazine.

2. The method of claim 1 wherein the alkali metal is lithium, sodium or potassium.

3. The method of claim 1 wherein step (a) is carried out with one equivalent of cyanuric chloride per 3.3 equivalents of sodium hydrosulfide.

4. The method of claim 1 wherein step (b) stirring is carried out for at least 1 hour.

5. The method of claim 1 wherein stirring is carried out at a temperature from 25° to 60° C.

6. The method of claim 1 wherein the temperature of the reaction mixture is maintained below 60° C.

7. The method of claim 1 wherein the acid used in step (d) is an inorganic mineral acid.

8. The method of claim 1 comprising the steps of:

(a) forming a reaction mixture of an acetone solution of cyanuric chloride and an aqueous solution of 3.3 equivalents of sodium hydrosulfide hydrates per equivalent of cyanuric acid;

(b) maintaining a temperature during mixing below 60° C.;

(c) stirring the mixture for at least 1 hour at temperature between 25° to 60° C. thereby forming 2,4,6-trimercapto-s-triazine;

(d) cooling the mixture to room temperature;

(e) acidifying the mixture with hydrochloric acid to form a precipitate; and (f) dissolving the precipitate in a potassium hydroxide thereby forming a tripotassium salt of 2,4,6 trimercapto-s-triazine.

9. A trialkali metal salt, other than sodium, or a triammonium salt of 2,4,6 trimercapto-s-triazine wherein said salts are sulfide free.

10. The salt of claim 9 wherein the alkali metal is lithium or potassium.

11. A sulfide free tripotassium salt of 2,4,6 trimercapto-s-triazine.

* * * * *